(12) United States Patent
Carlson (10) Patent No.: US 11,311,074 B2
(45) Date of Patent: Apr. 26, 2022

(54) ARCH SUPPORT SYSTEM

(71) Applicant: Michael A. Carlson, Redondo Beach, CA (US)

(72) Inventor: Michael A. Carlson, Redondo Beach, CA (US)

(*) Notice: Subject to any disclaimer, the term of this patent is extended or adjusted under 35 U.S.C. 154(b) by 17 days.

(21) Appl. No.: 16/373,528

(22) Filed: Apr. 2, 2019

(65) Prior Publication Data

US 2019/0307203 A1 Oct. 10, 2019

Related U.S. Application Data

(60) Provisional application No. 62/653,503, filed on Apr. 5, 2018.

(51) Int. Cl.
| | | |
|---|---|---|
| *A43B 7/14* | (2022.01) | |
| *A61F 5/01* | (2006.01) | |
| *A43B 7/142* | (2022.01) | |
| *A43B 7/1445* | (2022.01) | |

(52) U.S. Cl.
CPC ............ *A43B 7/142* (2013.01); *A43B 7/1445* (2013.01); *A61F 5/0111* (2013.01)

(58) Field of Classification Search
CPC ..... A43B 7/142; A43B 7/1445; A43B 7/1495; A43B 7/143; A61F 5/01111
See application file for complete search history.

(56) References Cited

U.S. PATENT DOCUMENTS

| | | | | |
|---|---|---|---|---|
| 987,599 | A * | 3/1911 | Quenzer | A61F 13/065 602/66 |
| 1,318,972 | A * | 10/1919 | Cook | A61F 13/065 602/66 |
| 1,443,844 | A * | 1/1923 | Jensen | A61F 13/066 602/66 |
| 1,627,596 | A | 5/1927 | Cutshaw | |
| 1,651,285 | A | 11/1927 | Levick, Jr. | |
| 1,785,185 | A * | 12/1930 | Day | A61F 5/019 602/30 |
| 2,358,966 | A * | 9/1944 | Einstoss | A61F 13/065 602/66 |
| 2,708,930 | A | 5/1955 | Lowman | |
| 3,316,663 | A * | 5/1967 | Neu | A43B 7/1435 36/71 |
| 3,722,113 | A * | 3/1973 | Birkenstock | A43B 7/146 36/11.5 |

(Continued)

FOREIGN PATENT DOCUMENTS

| | | |
|---|---|---|
| JP | 2008307196 A | 8/2012 |
| WO | WO 2014165964 A1 | 10/2014 |

OTHER PUBLICATIONS

First Examination Report, dated Mar. 12, 2020, issued by the Australian patent officefor patent application No. 2019202391.

(Continued)

*Primary Examiner* — Jila M Mohandesi
(74) *Attorney, Agent, or Firm* — Womble Bond Dickinson (US) LLP (57) ABSTRACT

An arch support comprising a first end that is inwardly curved in a distal direction; a second end that is outwardly curved in the distal direction, the second end is opposite to the first end; a middle portion connecting the first end and the second end, and wherein the first end, the second end and the middle portion are configured to support only an arch of a foot.

15 Claims, 9 Drawing Sheets

(56) References Cited

U.S. PATENT DOCUMENTS

| | | | |
|---|---|---|---|
| 4,392,487 A * | 7/1983 | Seiner | A61F 13/066 |
| | | | 602/27 |
| 4,495,942 A * | 1/1985 | Palumbo | A61F 13/066 |
| | | | 602/27 |
| 4,603,698 A * | 8/1986 | Guttmann Cherniak | |
| | | | A43B 7/1415 |
| | | | 36/162 |
| 5,015,427 A * | 5/1991 | Sosnow | A43B 7/14 |
| | | | 264/115 |
| 5,545,129 A * | 8/1996 | Snook | A61F 5/0111 |
| | | | 128/894 |
| 5,755,679 A * | 5/1998 | Seiner | A61F 5/0111 |
| | | | 602/27 |
| 5,840,053 A | 11/1998 | Roth | |
| D445,192 S | 7/2001 | Rodgers | |
| 6,585,674 B2 | 7/2003 | Toda | |
| 7,041,075 B2 | 5/2006 | Sullivan | |
| 7,740,603 B2 | 6/2010 | Shoukry | |
| 7,856,742 B2 * | 12/2010 | Nguyen | A61F 5/14 |
| | | | 36/155 |
| 8,162,868 B2 * | 4/2012 | Llorens | A61F 5/14 |
| | | | 602/28 |
| 8,240,066 B2 * | 8/2012 | Logan | A61F 5/0111 |
| | | | 36/91 |
| 2005/0251073 A1 * | 11/2005 | Roth | A61F 5/30 |
| | | | 602/8 |
| 2007/0074430 A1 * | 4/2007 | Coomer | A43B 7/1465 |
| | | | 36/145 |
| 2007/0283597 A1 | 12/2007 | Logan | |
| 2012/0311891 A1 | 12/2012 | Logan | |
| 2013/0025156 A1 * | 1/2013 | Martinez | A43B 7/1425 |
| | | | 36/43 |
| 2013/0066249 A1 | 3/2013 | Eldridge | |
| 2015/0335460 A1 * | 11/2015 | Weaver, II | A61F 5/01 |
| | | | 602/7 |
| 2019/0069628 A1 * | 3/2019 | Cutler | A43B 13/32 |

OTHER PUBLICATIONS

Second Examination Report, dated Nov. 4, 2020, issued by IP Australia for related Australian Patent Application No. 2019202391.

* cited by examiner

ARCH SUPPORT SYSTEM

CLAIM OF BENEFIT TO PRIOR APPLICATION

This application claims priority to U.S. Provisional Application 62/653,503, filed Apr. 5, 2018, the contents of which are incorporated herein by reference in its entirety.

FIELD

An embodiment of the disclosure relates to an arch support system that includes an arch support that rests under the arch of the foot to provide arch support and straps to secure the arch support to the foot. Other embodiments are also described.

BACKGROUND

A shoe is an item of footwear intended to protect and comfort the human foot while doing various activities. The design of shoes has varied enormously through time and from culture to culture, with appearance originally being tied to function. Contemporary footwear varies widely in style, complexity, and cost. Some shoes are designed for specific purposes. For example, some shoes are designed specifically for leisure activities, such as boots for mountaineering or skiing. While other shoes are designed to be worn as safety equipment, such as steel-toe boots which are required on construction sites.

SUMMARY

Along with protection and comfort, footwear may provide arch support for a person's foot. The anatomy and shape of the arch of the foot can vary from person to person. Those with high arches may need more support in the arch of the foot, while others with flat feet may need less support so as to avoid injury. Individuals with high arches may begin to suffer from plantar fasciitis if the proper support is not supplied to the arch of the foot. Thus, some people may need to wear shoes that provide the proper support at all times. This, however, may be incontinent when a person either wishes not to wear shoes (e.g., while relaxing at home), or wants to perform an activity where being barefoot is preferable and/or necessary. For example, water sports, such as paddleboarding, surfing, swimming, beach running, may require a person to be barefoot in order to give the person tactile sense of how, in the case of paddleboarding, the board is shifting in the water. Thus, there is a need for an arch sandal or arch support system that provides arch support while allowing the user to be practically barefoot.

The instant disclosure is directed to an arch sandal system with an arch sandal or support that provides proper arch support without confining the foot in a shoe. The system may include two arch supports or sandals, for example, one configured for the left foot and one configured for the right foot. Each arch support is configured to conform to the arch (which includes the medial, the lateral, and transverse arches) of the user's foot, while allowing a remainder of the foot (e.g., the heel, the ball of the foot, and/or the toes) to remain bare. The arch sandal or support includes a proximal end having a concave shape or inward curve toward a center of the support. The proximal end may be the end of the support which faces the user's heel therefore when placed on the foot, the support curves around the heel and does not cover the user's heel such that the user's heel is exposed. The sandal or support also includes a distal end having a convex shape or outward curve in a direction away from the center of the support. The distal end may be the end of the support which faces the users' toes, however, does not extend past the ball of the foot, leaving the ball of the foot and the toes exposed. Although curved ends are disclosed, it is contemplated that inwardly or outwardly extending ends may have other shapes (e.g., a polygon shape) suitable for conforming to the shape of the foot as disclosed herein. In addition, the arch support may be considered as having a medial side, which conforms to the medial portion of the arch or foot, and a lateral side, which conforms to the lateral portion of the arch or foot. In some aspects, the arch support may be thicker at the medial side than the lateral side, or said another way, tapers in a direction of the lateral side, and therefore considered to have a shape similar to that of the Nike® Swoosh®.

In one embodiment, one or more straps may be used to secure the arch support to the user's foot. For instance, a strap may be coupled to a lateral side of the arch support and another strap may be coupled to a medial side of the arch support. To secure the arch support to the foot, the straps may be wrapped around the user's ankle and tied together in a knot behind the ankle without any fastener (e.g., clip, snap, hook and loop fastener, etc). In addition, it should be understood that the straps may be attached to the arch support, and of a length suitable to be pulled up and then back around the ankle and tied at a position that is not aligned with, or otherwise considered directly over, the arch support. Rather, the tied ends are located behind the ankle and may therefore be considered tied behind the proximal end of the support (e.g., above the heel). The straps may be made of any material having some degree of stretch or elasticity. In this aspect, when wrapping the straps around the ankle, the user may pull at the straps to produce tension that pulls the arch support towards the sole (or arch) of the user's foot. As disclosed herein, the arch support system may include only the arch support and one or more straps, without any fasteners or other components, therefore provides a user friendly and effective way to provide support to the arch of the foot without a shoe.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the disclosure are illustrated by way of example and not by way of limitation in the figures of the accompanying drawings in which like references indicate similar elements. It should be noted that references to "an" or "one" embodiment in this disclosure are not necessarily to the same embodiment, and they mean at least one. Also, in the interest of conciseness and reducing the total number of figures, a given figure may be used to illustrate the features of more than one embodiment of the disclosure, and not all elements in the figure may be required for a given embodiment.

DETAILED DESCRIPTION

Several embodiments of the disclosure with reference to the appended drawings are now explained. Whenever the shapes, relative positions and other aspects of the parts described in the embodiments are not explicitly defined, the scope of the disclosure is not limited only to the parts shown, which are meant merely for the purpose of illustration. Also, while numerous details are set forth, it is understood that some embodiments of the disclosure may be practiced without these details. In other instances, structures and techniques have not been shown in detail so as not to obscure the understanding of this description. Furthermore, unless the meaning is clearly to the contrary, all ranges set forth herein are deemed to be inclusive of the endpoints. In addition, the terms "over", "to", and "on" as used herein may refer to a relative position of one feature with respect to other features. One feature "over" or "on" another feature or bonded "to" another feature may be directly in contact with the other feature or may have one or more intervening layers. In addition, the use of relative terms throughout the description, such as "top", "above or "upper" and "bottom", "under" or "lower" may denote a relative position or direction. For example, a "top edge", "top end" or "top side" may be directed in a first axial direction and a "bottom edge", "bottom end" or "bottom side" may be directed in a second direction opposite to the first axial direction.

As used herein, "medial" is a description of a human foot or of the arch sandal system that refers to being situated towards a median plane of a human body or closest to the medial arch of the foot with respect to the lateral arch. This is in contrast to a description of "lateral" that refers to being situated away from the median plane or being closest to the lateral arch of the foot with respect to the medial arch. As another example, in the context of the foot, a medial side refers to the "inside" of the foot, while a lateral side refers to the "outside" of the foot.

Figure 1:
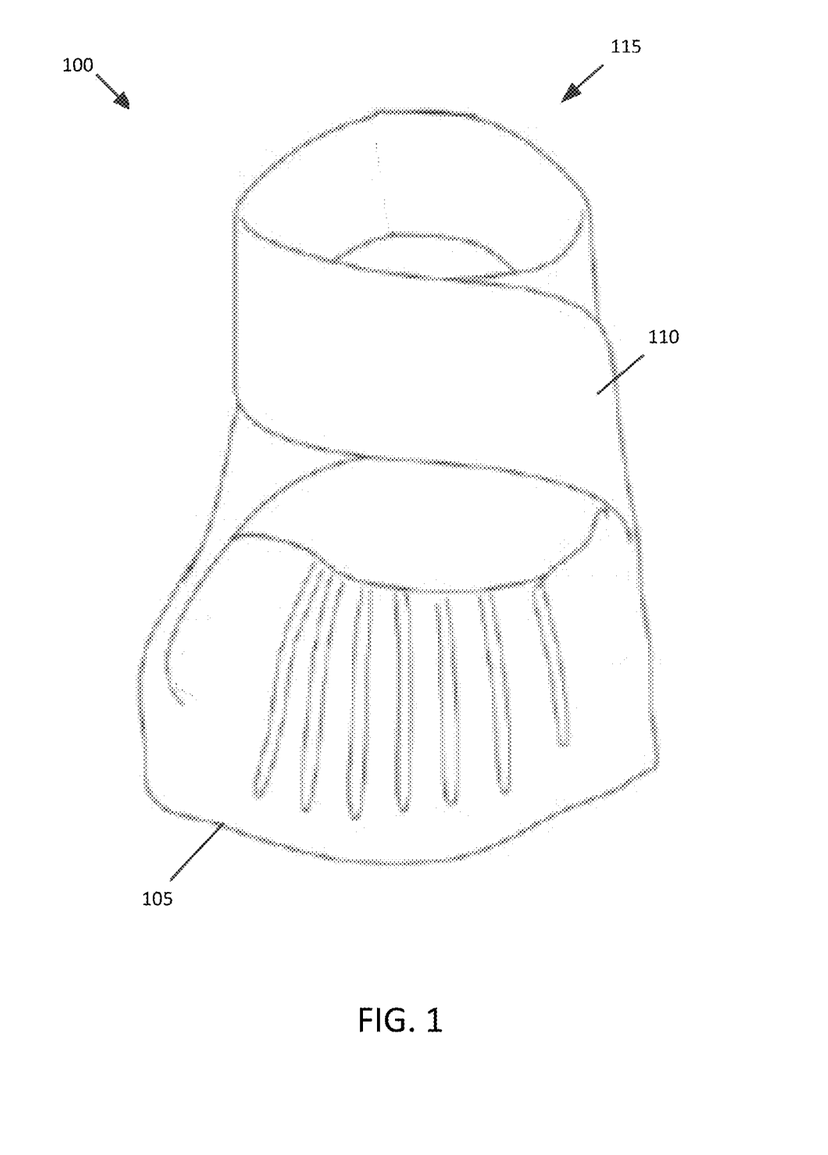
FIG. 1 is a front perspective view of an arch sandal system showing the inside of the arch support as well as one example of a strap configuration according to an embodiment of the present disclosure.

FIG. 1 illustrates a front perspective view of an arch support system 100 showing the inside of the arch sandal as well as one example of a strap configuration of one embodiment. The arch support system 100 includes an arch support (or arch sandal or support body) 105 and a strap 110. In one embodiment, the arch support 105 is configured to fit under the arch of a foot (or the midfoot) to provide arch support when for example standing. Specifically, the arch support 105 is said to support an arch of the foot by providing support (and therefore be in contact with) to at least one of the three arches of the foot that are formed by the tarsal and metatarsal bones (e.g., the medial arch, the lateral arch, and the transversal arch), while being worn by a user. Thus, in one embodiment, the arch support 105 is of a shape and size that allows it to be confined to only an area of the arch, and only support the arch of the foot. In another embodiment, the arch support 105 is configured to allow at least a portion of the sole of the foot to be bare when the sandal is secured to the user's foot. For example, the heel of the foot (or hindfoot) and/or the ball of the foot (or forefoot), which includes the five toes may be exposed (or bare). In one embodiment, the arch sandal may be configured to support less than a length of a foot that is to be supported by the sandal. Thus, the arch support 105 may provide proper arch support without confining the foot in a closed-type or open-type style footwear, where the sole of the foot including toes, ball, and heel are in contact with a bottom of the footwear.

The strap 110 is configured to secure the arch support 105 to the foot of the user. In one embodiment, the strap 110 includes one or more strips of material coupled to either side of the arch support 105 and a loop or end(s) 115 that extend behind the ankle. To secure the arch support 105 to the foot, the loop or end(s) 115 of the strap are configured to wrap around and tie (although not shown) behind an ankle of the user. In one embodiment, while worn by the user, the strap 110 does not rest upon (or come into contact) with a dorsal (or top) portion (or surface) of the foot. In one embodiment, the strap 110 is configured to have two or more straps that wrap around the ankle. The strap 110 secures the arch support 105 through tension put on the strap while the end(s) 115 wrap around the ankle. In particular, the strap 110 pulls the arch sandal upward and towards the sole of the foot when worn.

In one embodiment, the arch support 105 and the strap 110 of the system 100 may both be composed of the same or different materials. For example, the arch support 105 may be composed of at least one of a polymer (e.g., synthetic fiber), rubber, foam, and textile (e.g., cotton). In one embodiment, the arch support 105 is preferably composed of silicone due to its hypoallergenic properties. Similarly, the strap 110 may be composed of at least one of a polymer, rubber, and textile. The strap 110 may be made of any material having an elasticity, for example, a synthetic fiber made of an elastane fiber (e.g., Lycra®). In one embodiment, the arch support 105 and the strap 110 may be "machined" or produced from a mold as a single component. As a result, the strap 110 may be permanently coupled (e.g., not configured to detach) from the arch support 105. In another embodiment, at least one side of the strap that is coupled to the arch support is detachable from the support.

In another embodiment, the arch support 105 and the strap 110 are separately machined components. Specifically, the arch support 105 may be produced from a mold as a single piece of material, such as silicone. The strap 110 may than be configured to couple to the arch support 105. More about how the strap 110 couples to the arch support 105 is described herein.

Figure 2A:
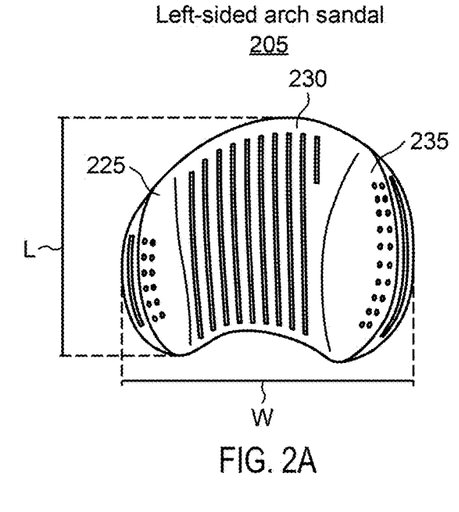
FIGS. 2A and 2B are top views of a pair of arch supports.
Figure 2B:
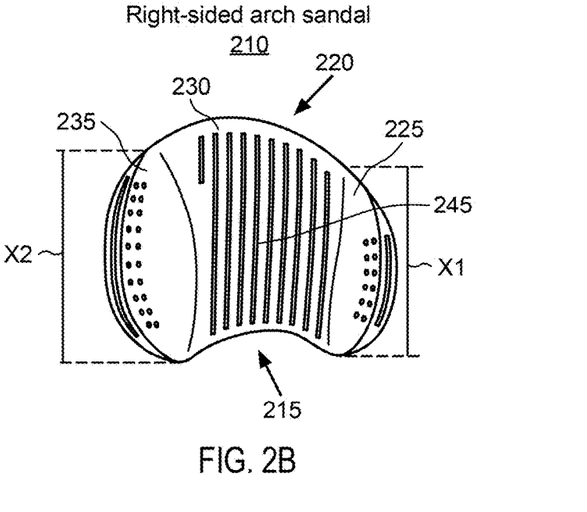

FIGS. 2A and 2B illustrate top views of a pair of arch supports. In particular, these figures show a top view of the left-sided arch support 205 and a top view of the right-sided arch support 210. In one embodiment, the support 205 (or 210) is the same or similar to the support 105 of FIG. 1. The support 205 is designated as "left-sided" because when worn by a user, this support is to be secured on the user's left foot. Similarly, support 210 is designated as "right-sided" because it is worn on the user's right foot. In one embodiment, the sandals 205 and 210 are not interchangeable. For instance, support 205 is not meant to be worn on a right foot, and support 210 is not meant to be worn on the left foot, due to its design.

Each of supports 205, 210 includes a first (or lateral) side (or portion) 225, a middle portion 230, and a second (or medial) side (or portion) 235. The middle portion 230 connects the first side 225 to the second side 235. In one aspect, the sides are coupled to the middle portion 230. In another embodiment, the first side 225, the middle portion 230, and the second side 235 are formed (or molded) as one continuous arch support body. Specifically, the arch support 205 may be formed from one mold, as previously described.

The support 205 has a length ("L") that reaches between a most proximal point of the middle portion 230 to a most distal point of (either) of the sides 225 and/or 235. The length ("L") may be within a range sufficient to support the arch of an adult size foot or an adolescent sized foot, as disclosed herein. For example, in one embodiment, L is between 50 millimeters and 150 millimeters, for example from 70 millimeters to 120 millimeters or from 85 millimeters to 100 millimeters. In one embodiment L is 90.5 millimeters. The support 205 has a width ("W") that reaches between a most lateral point of the lateral portion 225 to a most medial point of the medial portion 235. The width ("W") may be within a range sufficient to support the arch of an adult sized foot or an adolescent sized foot, as disclosed herein. For example, in one embodiment, W is between 60 millimeters to 160 millimeters, for example from 80 millimeters to 140 millimeters or from 100 millimeters to 120 millimeters. In one embodiment, W is 109 millimeters. The support 210 may have a similar length ("L") and width ("W") as support 205.

The support 205 includes a first (proximal) end 215 that is a curved inwardly toward the center 245, or considered to have a concave shape. This end is rounded such that it forms a continuous inward curve from the lateral portion 225 to the medial portion 235, although other shapes may be used (e.g., polygon). In one embodiment, the first end 215 is configured to form around, and expose a heel of the foot of the user. The support 205 also includes a rounded second (or distal) end 220. This end is rounded such that it curves away from (or in a distal direction) the center 245 of support 205. For example, end 220 may be considered to have a convex shape. This end 220 is an opposite end of the first end 215. In one embodiment, end 220 is configured to support the midfoot of a user. More specifically, the end 220 is configured to at least partially support the transversal arch. In one embodiment, the end 220 may support a portion of the ball of the foot. In one embodiment, the support 205 may include either (or both) arched ends 215 and 220.

In one embodiment, the lateral side 225 is configured to conform to a lateral side of a foot when worn by a user. Specifically, the outside of the user's foot rests upon the lateral portion 225. Similarly, the medial side 235 is configured to conform to a medial side of the foot when worn by the user. Thus, the outside of the user's foot rest upon the medial portion 225. In one embodiment, both sides are rounded away from the support 205. In another embodiment, the sides may have any shape (e.g., the sides may be straight). In one embodiment, both sides have different lengths. For instance, the lateral side 225 has a first length ("X1") and the medial side 235 has a second length ("X2"). In one embodiment, the length of X1 is less than X2. In another embodiment, both lengths may be the same or X2 may be shorter than X1. Representatively, in one embodiment, the length of X1 may be from about 55 millimeters to about 80 millimeters, for example, from about 60 millimeters to about 75 millimeters, or from about 64 millimeters to about 72 millimeters. In addition, X2 may be from about 70 millimeters to about 85 millimeters, or from about 72 millimeters to about 81 millimeters. For example, in one embodiment, X1 may be between 71-72 millimeters and X2 may be 80-81 millimeters, alternatively X1 and X2 may be approximately 10 percent less, for example, X1 may be between 64-65 millimeters and X2 may be between 72-73 millimeters.

Figure 3A:
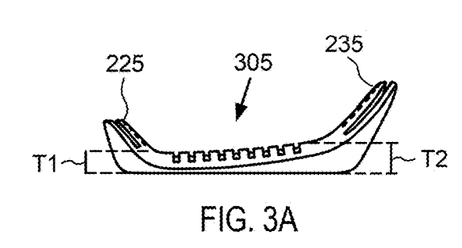
FIGS. 3A and 3B are back views of a pair of arch supports.
Figure 3B:
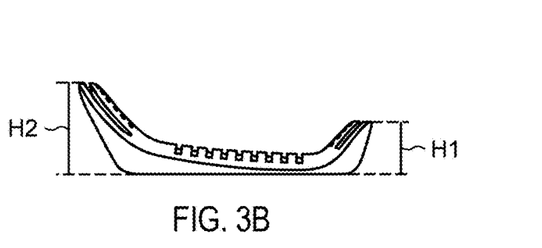

FIGS. 3A and 3B illustrate back end views of the pair of arch supports 205 and 210. In particular, from this view, it can be seen that a thickness of the arch support 205 tapers from the second side 235 to the first side 225. The support 205 has a thickness ("T1") that reaches from a top surface of the support 205 (or middle portion 230) to a bottom surface of the support 205. In one embodiment, T1 is a cross-sectional measurement of a first side of the middle portion 230 that is next to the lateral side 225. In another embodiment, T1 is a cross-sectional measurement of the lateral side 225. The support 205 also has a thickness ("T2") that reaches from the top surface of the support 205 (or middle portion 230) to the bottom surface of the support 205. In one embodiment, T2 is a cross-sectional measurement of a second side of the middle portion 230 that is next to the medial side 225 or is a cross sectional measurement of the medial side 235. As shown, T1 is thinner (or has less thickness) than T2. Representatively, T1 may be from about 5 millimeters to about 10 millimeters, or from about 7 millimeters to about 8 millimeters. In addition, T2 may be from about 8 millimeters to about 15 millimeters, or from about 10 millimeters to about 12 millimeters. For example, in one embodiment, T1 may be between 8-9 millimeters and T2 may be between 11-12 millimeters, or 10 percent less, for example T1 may be between 7-8 millimeters and T2 may be between 10-11 millimeters.

As shown in these figures, the support 205 is formed to fit the arch of a foot. Specifically, the lateral side 225 and the medial side 235 curve upward and away from each other to form around (and under) the arch of the foot. In one embodiment, the lateral side 225 and the medial side have curves with different angles. In another embodiment, they are angled the same. The lateral side 225 has a height ("H1") that reaches from a top surface of the side 225 to the bottom surface of the sandal. The medial side 235 has a height ("H2") that reaches from a top surface of the side 235 to the bottom surface of the sandal. H1 may be between 10 millimeters and 30 millimeters, for example, from about 18 millimeters to about 21 millimeters. H2 may be between 15 millimeters to 55 millimeters, for example from 22 millimeters to 48 millimeters or from 30 millimeters to 40 millimeters. In one embodiment, H1 is about 20 millimeters and H2 is 35 millimeters, or H1 and H2 may be about ten percent less. As shown, H1 is shorter (or has a lesser height) than H2. In this aspect, the lateral side 225 (having height H1) may be considered to be shorter than the medial side 235 (having height H2). In other embodiments, H2 may be shorter than H1.

This figure further illustrates that the top surface (or side) of the support 205 is a textured surface 305. Specifically, the middle portion 230 includes ridges that run from the first end 215 to the second end 220. In one aspect, the middle portion 230 includes ridges that run from either side and end before reaching the other side. In one embodiment, the textured surface 305 may comprise may be any texture, such as nubs that extend upward from the top surface of the support 205.

Figure 4A:
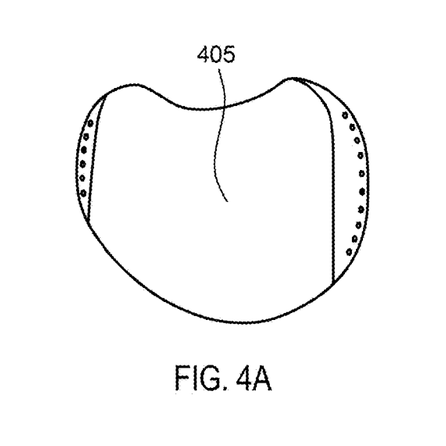
FIGS. 4A and 4B are bottom views of a pair of arch supports.
Figure 4B:
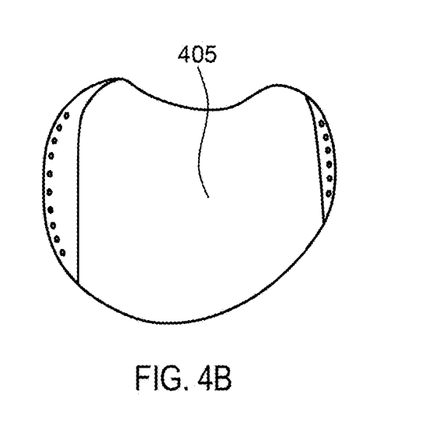

This textured surface 305 provides slip prevention that prevents a user's foot from changing positions while the support 205 is being worn. Similarly, the bottom of the sandals may be textured. For example, FIGS. 4A and 4B illustrate bottom views of the pair of arch sandals 205 and 210. In particular, from this view, it can be seen that the bottom surface (or side) of both sandals is a textured bottom surface 405. Specifically, the sandal has a textured pattern of nubs and ridges that run widthwise to the sandals. In one embodiment, similar to the top textured surface 305, the bottom surface 405 may comprise any texture. This surface 405 increases traction on slick surfaces in order to prevent the arch support 205 from shifting while supporting the foot on such surfaces.

Figure 5A:
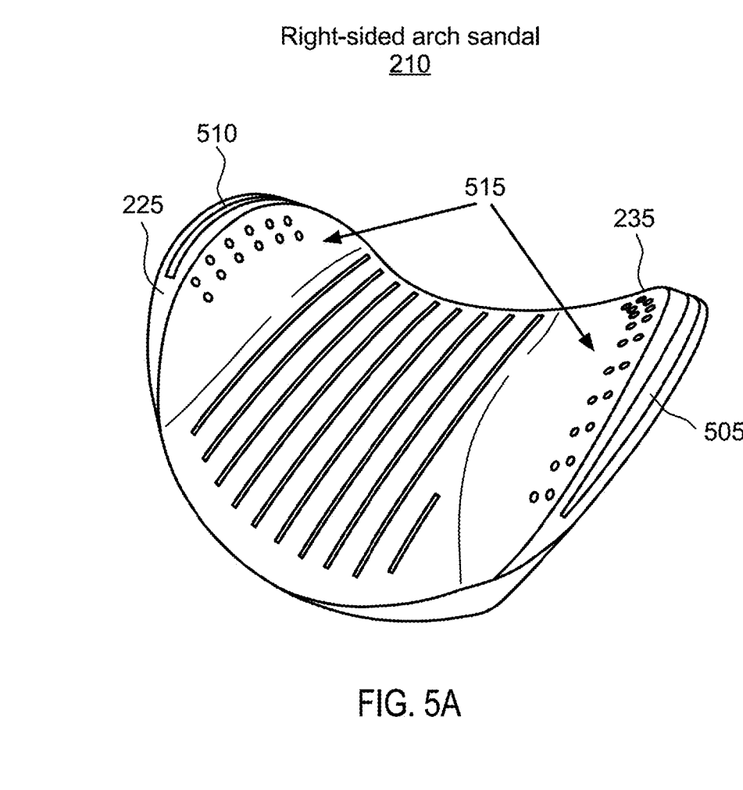
FIGS. 5A and 5B are front perspective views of a pair of arch supports.
Figure 5B:
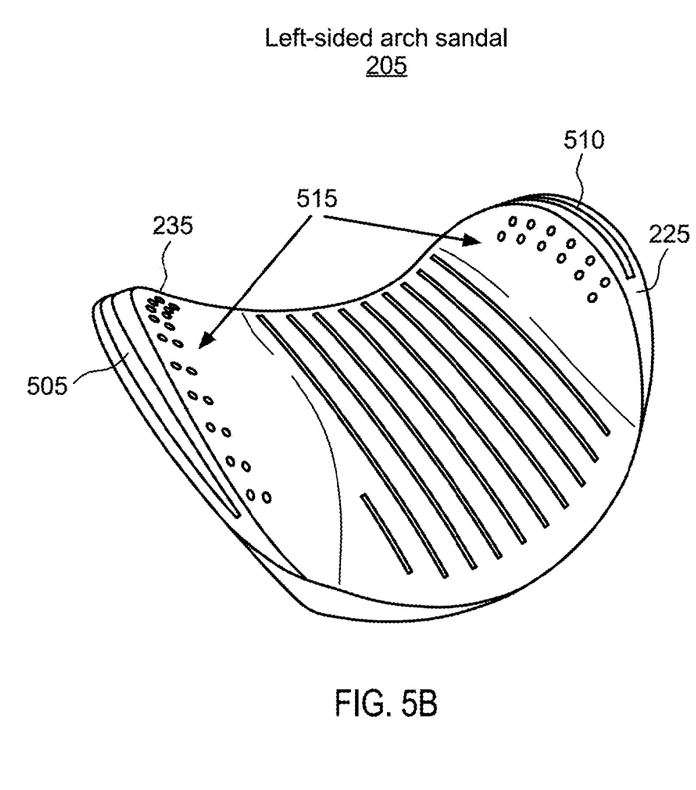

FIGS. 5A and 5B illustrate front perspective views of the pair of arch supports 205 and 210. As previously described, the arch supports of the present may couple to one or more straps. These figures show a configuration that allows the arch support 205 to couple to one or more straps. For example, in one aspect, the lateral side 225 and the medial side 235 of each support 205 and 210 include openings or slots for insertion of the straps. For instance, the lateral side 225 includes a first opening or slot 510 that runs along at least a portion of an outward facing surface of the lateral side and is configured to receive a portion of a (e.g., first) strap. Similarly, the medial side 235 includes a second opening or slot that runs along at least a portion of an outward facing surface of the medial side and is configured to receive a portion of a (e.g., second) strap. In one embodiment, the first opening is smaller (e.g., has a length that is less) than the second opening. As will be described herein, the difference between the two openings allows different sized straps to be coupled therein. In another embodiment, the openings are the same size (and length).

FIGS. 5A and 5B also show that the lateral side 225 and the medial side each include one or more holes 515 that open onto the top surface (e.g., the surface that supports the user's foot) of each side. Specifically, the lateral side 225 includes two rows of holes, each row having six holes. The medial side includes two rows of holes, each row having ten holes. In one embodiment, both sides may have a similar or same number of holes. In one embodiment, the holes 515 traverse through each side, from a top surface, into a respective opening, and out of a bottom surface. In another embodiment, at least one side's holes traverse through the side's surface and into its respective opening.

Figure 6A:
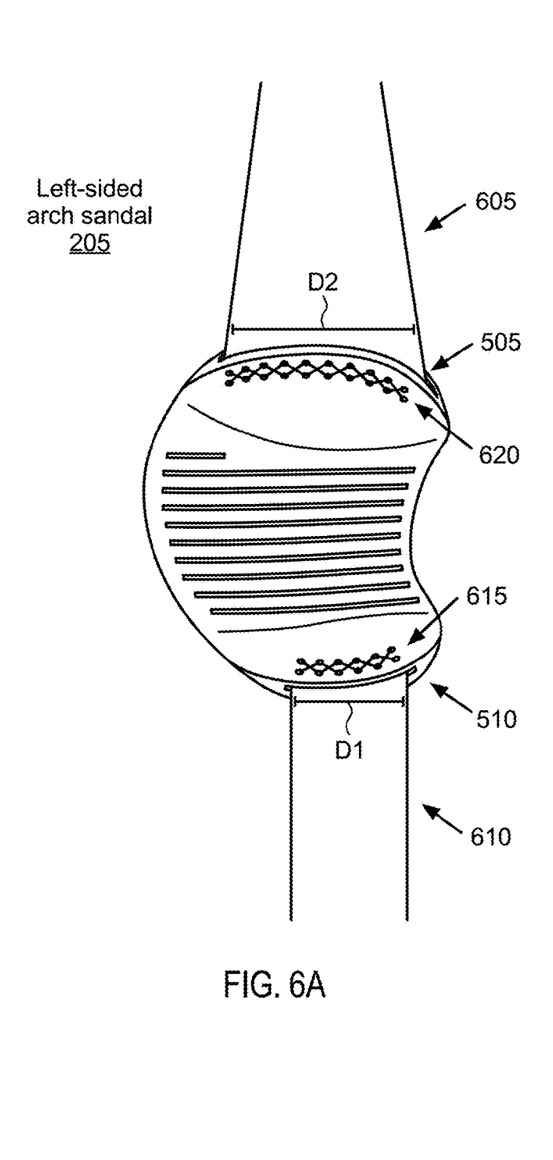
FIGS. 6A and 6B are top views of a pair of arch support systems that each show an arch support with straps that are laid flat.
Figure 6B:
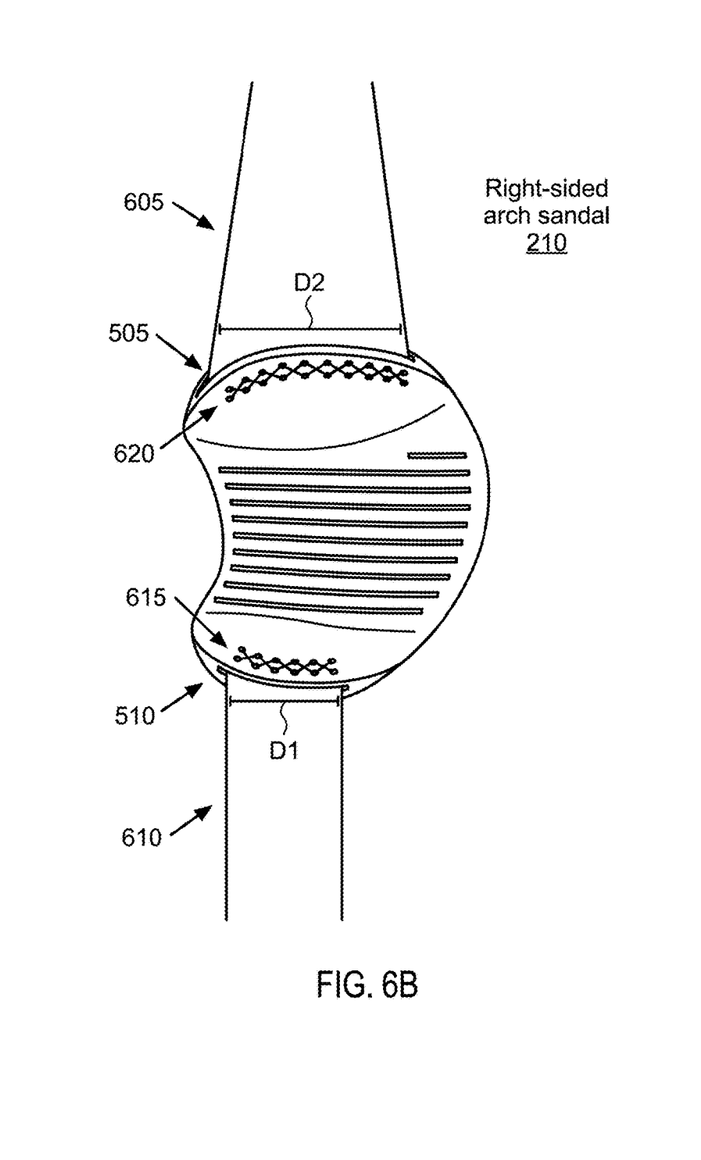

FIGS. 6A and 6B illustrate top views of the pair of arch supports 205 and 210 with straps coupled thereon that are laid flat. These figures illustrate straps coupled to the arch support according to the configuration illustrated in FIGS. 5A and 5B. FIGS. 6A and 6B show that a (e.g., first) strap 610 is coupled to the lateral side 225. In particular, the opening 510 is receiving a portion of the strap 610. The strap is attached to the side through stitching 615. In one embodiment, a piece of thread is used to stitch the strap to the side 225. The stitching goes through the holes 515 (illustrated in FIGS. 5A and 5B). In another embodiment, the thread used to stitch is composed of the same or similar material as the strap 610. Similarly, the (e.g., second) strap 605 is coupled to the medial side 235 by attaching the strap 605 to the side through stitching 620. In one embodiment, the straps may be coupled to their respective sides differently. For example, the straps may be attached to the support through the use of buttons, buckles, a hook and loop system, or the like.

FIGS. 6A and 6B also illustrate that the straps are of different widths. The first strap 610 has a (e.g., first) width ("D1") that is at least or less than the length of the opening 510 in order to allow the opening 510 to receive the strap 610. In one embodiment, the width D1 is uniform along a length of the first strap 610. For example, D1 may be from 20 millimeters to 40 millimeters, for example, from about 30 millimeters to about 32 millimeters. In another embodiment, the width D1 may vary. The second strap 605 has a (e.g., second) width ("D2") that is at least or less than the length of the opening 505 in order to allow the opening 505 to receive the strap 605. In one embodiment, the width D2 varies (or tappers as it moves) away from the portion that is received by the opening 505. Thus, D2 decreases as the strap moves away from the opening 505. D2 near the attachment point to the support member may be from about 45 millimeters to about 60 millimeters, for example, from about 50 millimeters to about 56 millimeters. In one embodiment, D2 of strap 605 is (e.g., always) greater than D1 of strap 610. In another embodiment, D2 of strap 605 tapers until its width reaches the width of D1. In addition, it can be seen from these views that the strap 610 attached to the lateral side of the support is attached toward a proximal end of the support (end facing the heel), and the support generally curves toward the proximal end of the foot, so that the strap is towards the back of the foot, which provides a more secure fit.

In the illustrated embodiment, straps 605 and 610 are separate from each other, and in order to secure the arch support to a user's foot, both straps are configured to be tied together. In other embodiments, straps 605 and 610 may be one continuous strap.

Figure 7:
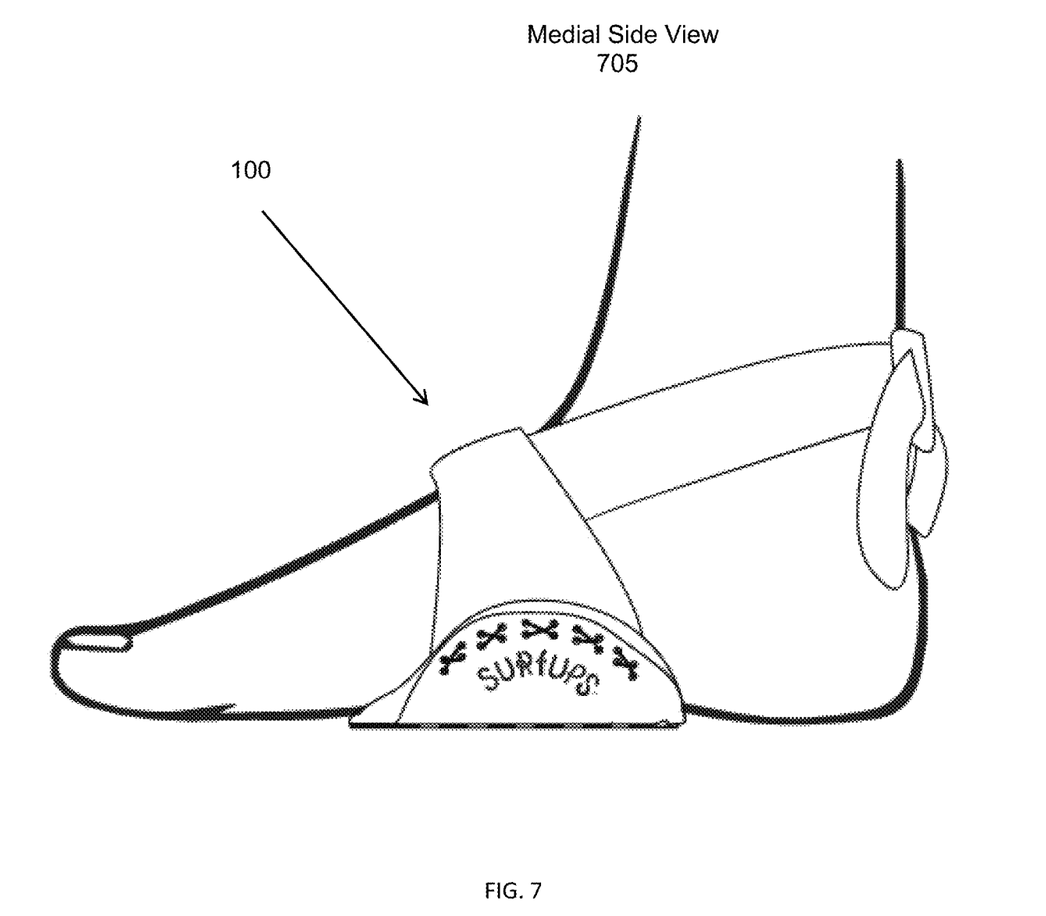
FIG. 7 shows a perspective view illustrating the medial side of the arch support system while being worn by a user.
Figure 8:
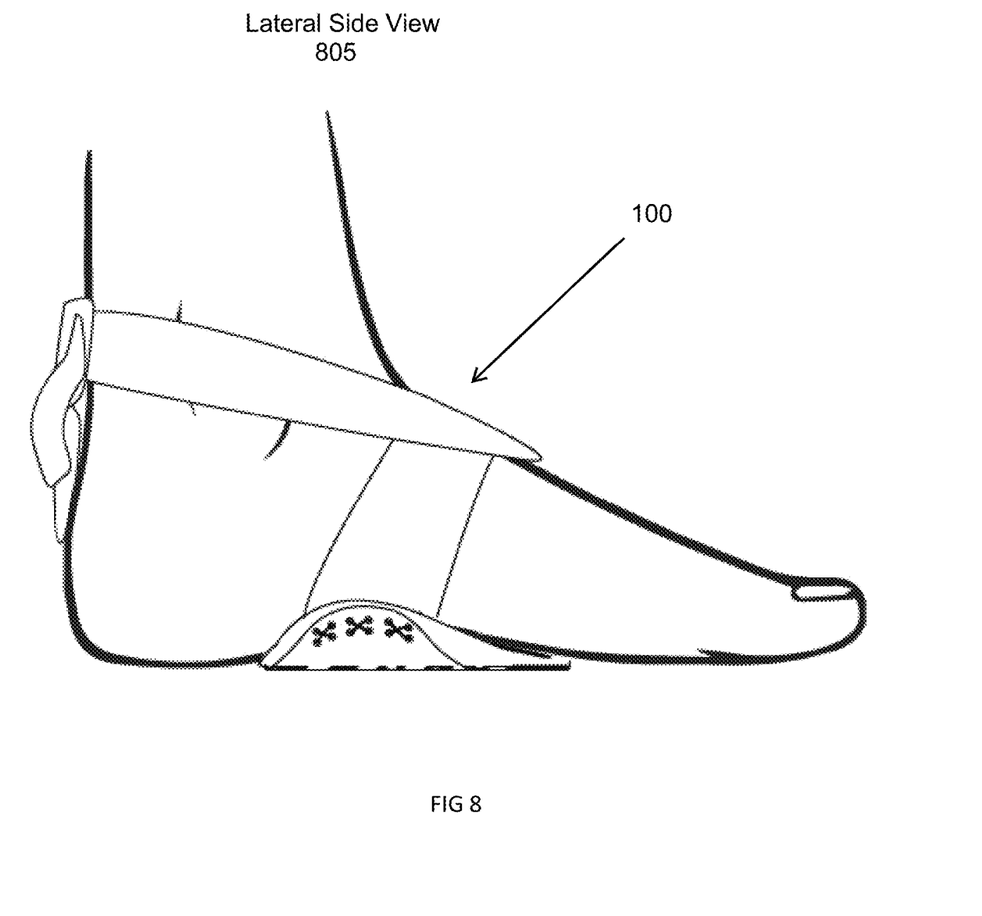
FIG. 8 shows a perspective view illustrating the lateral side of the arch support system while being worn by a user.
Figure 9:
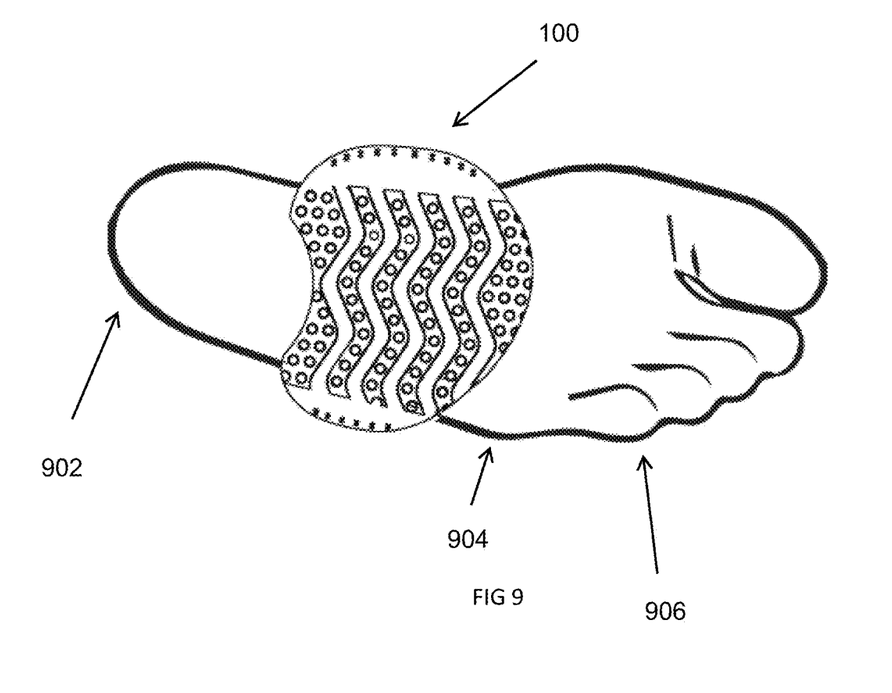
FIG. 9 shows a bottom view of the arch sandal system while being worn by a user.

FIGS. 7-9 illustrate different perspective views of the arch support system according to one embodiment of the present disclosure. For example, FIG. 7 shows a perspective view illustrating a medial side 705 of the arch support system while being worn by a user. In particular, this figure shows a user's foot inside the system 100, while straps of the system are wrapped around the ankle of the user. In some embodiments, the support may include vent, for example, channels that traverse (or run) through the medial side 235. In one embodiment, the lateral side 225 (not shown in this figure) may also include (the same or different number of) vents. These vents may be configured to allow water, debris, etc. to pass outside from between the user's sole and the top surface of the arch sandal.

FIG. 8 illustrates a lateral side view 805. From the lateral side view, it can be seen that the strap attached to the lateral side of the support extends along the outside of the foot, between the outer curved part of the foot (e.g., outer arch) and the heel (e.g., meaty portion of the heel). FIG. 9 illustrates a bottom view of the arch sandal system while being worn by the user. From this view, it can be seen that when the arch support is placed on the bottom of the foot, the majority of the foot, including the heel 902, ball of the foot 904 and toes 906, are exposed and remain uncovered by the support. In addition, it can be seen how the inward curve at the distal end of the support curves around the heel 902 so that the heel 902 remains exposed.

Figure 10:
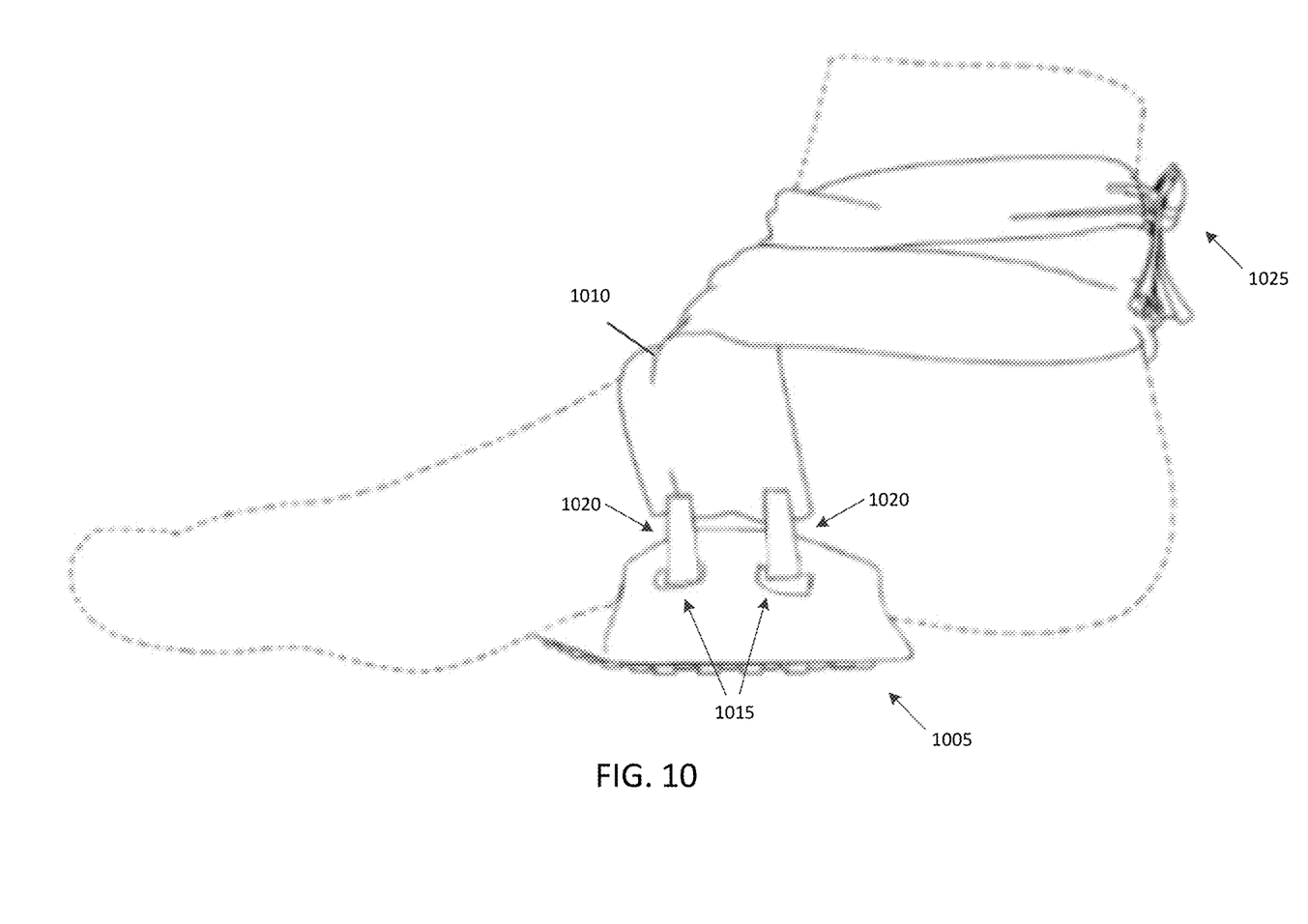
FIG. 10 shows a side view illustrating the medial side of another arch support system while being worn by a user.
Figure 11:
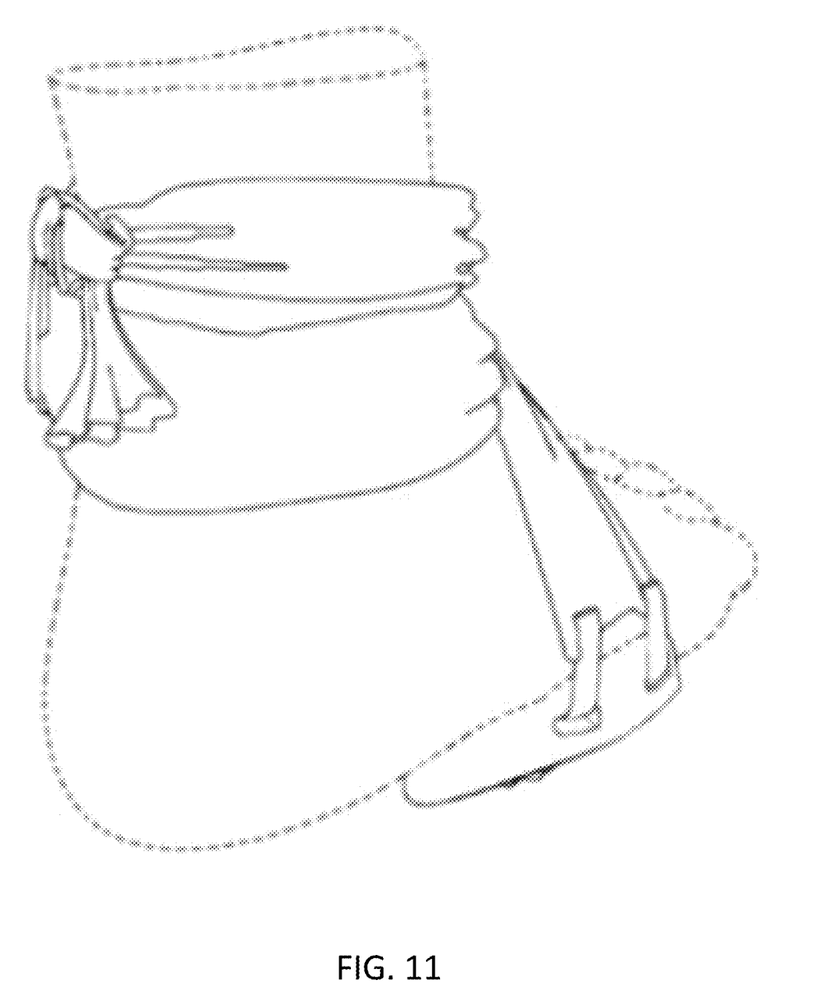
FIG. 11 shows a back perspective view illustrating the lateral side of the arch support system of FIG. 10.

FIGS. 10-11 illustrate additional perspective views of the arch support system according to another embodiment of the present disclosure. Specifically, these figures illustrate another configuration that allows an arch support to couple to one or more straps. As shown in FIG. 10, a strap 1010 is coupled to an arch support 1005 through the use of two separate straps (or clips) 1020. The arch support or more specifically the medial side of the arch support includes two holes 1015, which are configured to receive and couple to the straps 1020. In one embodiment, the straps 1020 are made of the same material as the strap 1010 that secures the sandal 1005 to the user's foot. The straps 1020 are configured to couple to the strap 1010. Thus, the strap 1010 couples to the arch support 1005 through the straps 1020. As shown, the straps 1020 are smaller than the strap 1010. This figure also illustrates that the strap 1010 secures the arch sandal 1005 by wrapping around the ankle of the user and being tied together with a knot 1025. FIG. 11 illustrates a back perspective view of the arch support system of FIG. 10 while being worn by the user.

In one embodiment, the description of the arch sandal system herein may relate to both the left-sided arch sandal system and the right-sided arch sandal system. For example, the description of the arch support 205 may also correspond to the arch support 210. The difference being that the arch support 205 is configured oppositely than the arch support 210 in order to accommodate a user's left foot. Thus, it should be understood that any description of the arch sandal system relates to both the left-sided system and the right-sided system. In addition, it should be understood that while specific dimensions are disclosed, they may vary within a range of about 10 percent. For example, in one aspect, the arch support system may be a full sized system with dimensions suitable for an adult male, and in other embodiments, the arch support system may have dimensions approximately 10 percent less than that of the full sized system such that it is suitable for use on a smaller foot, for example, a female or adolescent sized foot.

While certain embodiments have been described and shown in the accompanying drawings, it is to be understood that such embodiments are merely illustrative of and not restrictive on the broad disclosure, and that the disclosure is not limited to the specific constructions and arrangements shown and described, since various other modifications may occur to those of ordinary skill in the art.

What is claimed is:

1. An arch support comprising:
a first end having a continuous inward curve in a distal direction;
a second end having a continuous outward curve in the distal direction, the second end is proximal to the first end;
a middle portion connecting the first end and the second end, the middle portion having a top surface comprising ridges that run from the first end to the second end, a bottom surface having ridges that run from a first side to a second side of the middle portion, a thickness defined by the top surface and the bottom surface that increases from the first side to the second side, and wherein the first side curves upward and away from the second side and is configured to conform to a lateral side of the foot and has a first height and a first length, the second side curves upward and away from the second side and is configured to conform to a medial side of the foot and has a second height and a second length, and wherein the second height is greater than the first height and the second length is greater than the first length, and wherein the first end, the second end and the middle portion are configured to support only an arch of a foot;
a fastening member coupled to the first side or the second side; and
a strap coupled to the fastening member to attach the strap to the middle portion, and wherein the strap is a single continuous strap dimensioned to cross over a top of the foot and around an ankle of the foot to secure the arch support body to the foot.

2. The arch support of claim 1 wherein the middle portion connects the first side to the second side, wherein the first side, the middle portion, and the second side are one continuous structure.

3. The arch support of claim 1, wherein the fastening member comprises a buckle.

4. The arch support of claim 1, wherein the first end, the second end and the middle portion are made of at least one of silicone, rubber, and foam.

5. An arch support comprising:
an arch support body having a top surface and a bottom surface that define a thickness of the arch body support, wherein the bottom surface is substantially planar and comprises a series of ridges, the top surface comprises a series of ridges running in a different direction than the ridges of the bottom surface, and the thickness tapers from a medial side that is configured to support a medial portion of a foot to a lateral side that is configured to support a lateral portion of the foot, wherein the medial side is thicker than the lateral side and the medial side is longer than the lateral side, and a first slot dimensioned for attachment of a strap is formed in the medial side and a second slot dimensioned for attachment of a strap is formed in the lateral side, wherein the arch support body is configured to support less than an entire length of the foot that is to be supported by the arch support body and wherein the lateral side curves upward and away from the medial side to define a first height and the medial side curves upward and away from the lateral side to define a second height, wherein the first height is less than the second height.

6. The arch support of claim 5, wherein the arch support body has a proximal end that curves inward towards a center of the body and extends from the medial side of the body to the lateral side of the body.

7. The arch support of claim 5, wherein the arch support body has a distal end that curves outward from a center of the body and connects the medial side of the body to the lateral side of the body.

8. The arch support of claim 5, wherein at least one of the medial side and the lateral side has at least one vent that runs through the at least one of the medial side and the lateral side.

9. An arch support system comprising
an arch support body that is configured to provide arch support for a foot of a user, the arch support body includes a lateral portion, a middle portion, and a medial portion, wherein the middle portion is in between the lateral portion and the medial portion and comprises a thickness that tapers from the medial portion to the lateral portion, the lateral portion and the medial portion curve upward and away from each other to a lateral end and a medial end, respectively, and a height of the lateral end is less than a height of the medial end, and the arch support body has a length defined by a most proximal point of the middle portion to a most distal point of the lateral portion or the medial portion that is less than the foot the arch support body is configured to support, and the medial portion comprises a length that is greater than a length of the lateral portion;
a first strap coupled to the lateral portion by a fastening member at the lateral portion; and
a second strap coupled to the medial portion by a fastening member at the medial portion, wherein the first strap and second strap have different widths and are configured to cross one another over a top of the foot and wrap around an ankle of the user in order to secure the arch support body to the foot.

10. The arch support system of claim 9, wherein the lateral portion has a first opening that runs along a surface of the lateral portion and is configured to receive a portion of the first strap,
wherein the medial portion has a second opening that runs along a surface of the medial portion and is configured to receive a portion of the second strap.

11. The arch support system of claim 10, wherein the portion of the first strap that is to be received by the first opening of the lateral portion has a first width and the portion of the second strap that is to be received by the second opening of the medial portion has a second width.

12. The arch support system of claim 11, wherein the first width is uniform along a length of the first strap.

13. The arch support system of claim 9, wherein the first strap and the second strap are dimensioned to tie together behind the ankle.

14. The arch support system of claim 9, wherein the first strap and the second strap are tied together at a position that is behind the arch support body.

15. The arch support system of claim 9, wherein the straps are each composed of at least one of a synthetic fiber, rubber, and cotton.

* * * * *